United States Patent [19]

Bucalo

[11] 4,104,127
[45] Aug. 1, 1978

[54] ARTICLE FOR GROWING CULTURES IN A BODY CAVITY IN THE PRESENCE OF GAS, AND PACKAGE FOR THE ARTICLE

[76] Inventor: Louis Bucalo, 155 Roberts St., Holbrook, N.Y. 11741

[21] Appl. No.: 698,470

[22] Filed: Jun. 18, 1976

Related U.S. Application Data

[62] Division of Ser. No. 478,706, Jun. 12, 1974, Pat. No. 3,979,263.

[51] Int. Cl.² ............................ C12K 1/04; C12K 1/10
[52] U.S. Cl. ....................................... 195/127; 195/139
[58] Field of Search ...................... 195/103.5, 127, 139, 195/103.5 R, 103.5 M

[56] References Cited

U.S. PATENT DOCUMENTS

| | | | |
|---|---|---|---|
| 2,904,474 | 9/1959 | Förg | 195/103.5 R |
| 3,842,166 | 10/1974 | Bucalo | 195/103.5 M |
| 3,864,213 | 2/1975 | Bucalo | 195/139 |
| 3,979,263 | 9/1976 | Bucalo | 195/103.5 R |

Primary Examiner—Raymond N. Jones
Assistant Examiner—Robert J. Warden
Attorney, Agent, or Firm—Steinberg & Blake

[57] ABSTRACT

Cultures of microorganisms can be grown in a body cavity by situating therein a nutrient on a suitable carrier while maintaining the nutrient exposed to a predetermined gaseous atmosphere, so that microorganisms which require a particular atmosphere can grow directly in the body cavity on the nutrient. After a time sufficient for culture growth the carrier with the nutrient thereon are removed from the body cavity and inspected, for example, under a microscope with suitable dyes being used to stain the growth for rendering the latter easily visible. The carrier for the nutrient may take the form of a plastic sheet material having small protuberances which are thicker than a nutrient layer carried by the plastic sheet material and which serve to maintain apart from each other surfaces of the plastic and nutrient which otherwise might engage each other to prevent exposure of the nutrient to the predetermined atmosphere. The article is preferably packaged in a container which has in its interior sufficient moisture to prevent drying of the nutrient, the interior of the container being closed off from the outer atmosphere by the sheet material which is used for the container.

38 Claims, 25 Drawing Figures

ARTICLE FOR GROWING CULTURES IN A BODY CAVITY IN THE PRESENCE OF GAS, AND PACKAGE FOR THE ARTICLE

CROSS REFERENCE TO RELATED APPLICATIONS

This application is a division of copending application Ser. No. 478,706, filed June 12, 1974 now U.S. Pat. No. 3,979,263.

BACKGROUND OF THE INVENTION

Proposals have already been made for growing cultures directly in a body cavity. A number of advantages are achieved in this way. Thus, for example, the microorganisms grow under conditions precisely the same as those occurring in the body, and all of the disadvantages resulting from transferring with a suitable swab, for example, a body fluid which is suspected of carrying microorganisms out of the body onto a suitable growth medium, with artificial incubation, are eliminated.

However, it has been found that certain microorganisms require particular atmospheres for optimum growth conditions. For example, microorganisms associated with such diseases as gonorrhea, vaginitis, and other diseases which occur in body cavities, grow best when exposed to air.

In addition, during the interval between manufacturing articles for growing cultures in the body and use thereof, it is possible for the nutrient to become too dry to be fully effective.

Furthermore, some body cavities in which it is desirable to grow cultures are of extremely small dimensions creating special problems in connection with culture growth in such body cavities where the internal space is greatly restricted.

SUMMARY OF THE INVENTION

It is accordingly a primary object of the present invention to provide an article which assures the growth of a culture in a body cavity in such a way that exposure to a given gas is reliably maintained.

Thus, it is an object of the present invention to make it possible to prevent a nutrient in which a culture will grow when in the presence of an oxygen-containing atmosphere such as air from being closed off from the surrounding air which contains the oxygen which provides the best possible growing conditions for the microorganisms whose presence is suspected.

Furthermore, it is an object of the invention to provide an article of the above type which is relatively simple and inexpensive and which at the same time is highly reliable for achievement of the desired results.

Also it is an object of the present invention to provide an article which makes it possible to grow cultures in an extremely restricted area such as within a male urethra.

Furthermore, it is an object of the present invention to provide a package which will store a nutrient-carrying article in such a way that a long shelf life for the packaged article is assured without risking the possibility of the nutrient becoming too dry to remain effective.

Also it is an object of the present invention to provide an article of the above general type which makes inspection of growths highly effective by the use of suitable staining dyes which can be applied very readily with the articles of the invention.

According to the invention a nutrient for a microorganism is supported on a carrier which is then situated together with the nutrient in a body cavity where the nutrient is contacted with a body fluid which is suspected of having therein a microorganism which will grow in the nutrient. The nutrient which is placed in this way in the body cavity is maintained exposed to a predetermined gas so that a microorganism which requires the predetermined gas will grow in the nutrient. After a given time which is sufficient for growth of the microorganism in the nutrient to an extent adequate to render the microorganism visible, the carrier with the nutrient thereon are removed from the body cavity and checked for the presence of the microorganism. The carrier may be in the form of a sheet means such as a plastic sheet material which on one face carries the nutrient in the form of a layer. This sheet means is provided with protuberances which form a spacer means enabling the nutrient layer to be maintained exposed to the predetermined gaseous atmosphere by preventing turns or layers of the plastic sheet material and the nutrient thereon from directly engaging each other.

An example of a nutrient as referred to above is the following:

| Stuart Martin Medium extra additives to medium for gonorrhea | |
|---|---|
| 2 gram/liter Hemoglobin FORMULA Grams Added per Liter | |
| GBI Peptone 180 (Meat-Casein Polypeptone | 15.0 |
| Corn Starch | 1.0 |
| Dipotassium Phosphate (K$_2$HPO$_4$) | 4.0 |
| Monopotassium Phosphate (KH$_2$PO$_4$) | 1.0 |
| Sodium Chloride (NaCl) | 5.0 |
| Dextrose | 1.5 |
| Trimethoprim | 0.005 |

The above is a special nutrient added to the agar to grow gonococcus.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
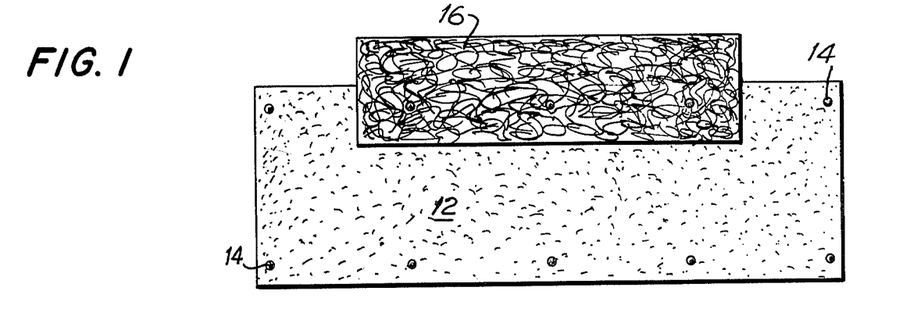
FIG. 1 is a schematic plan view of one possible article according to the invention before it assumes its final configuration where it is ready for use.
Figures 2, 3, 6, 19:
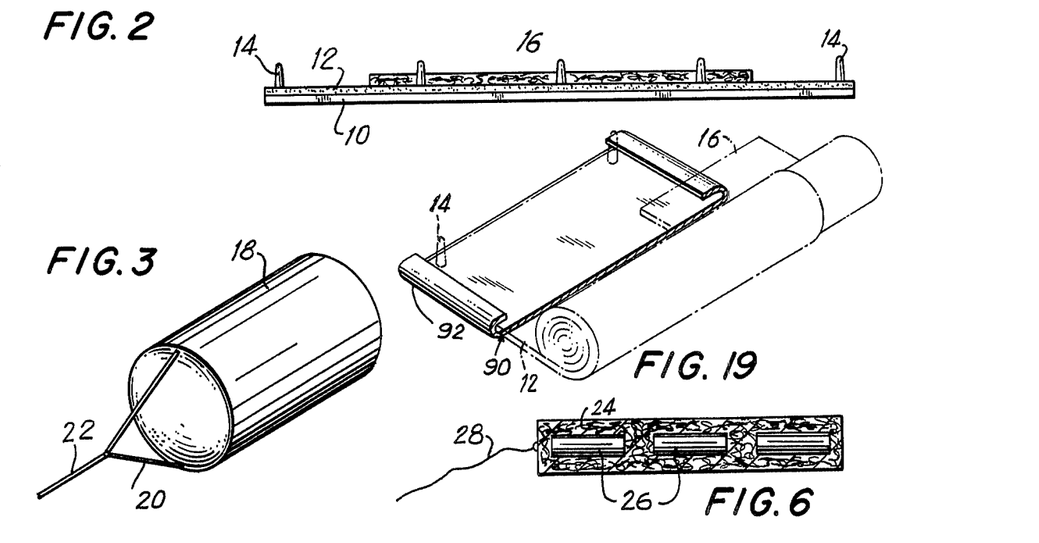
FIG. 2 is a side elevation of the structure shown in FIG. 1.
FIG. 3 is a perspective illustration of one possible embodiment of a structure for holding the assemblies of FIGS. 1 and 2 in a position suitable for use.
FIG. 6 is a schematic representation of the manner in which a plurality of articles of the invention may be simultaneously used.
FIG. 19 is a perspective illustration of a further embodiment of a structure for holding a nutrient layer in a flat condition for inspection purposes.

Referring first to FIGS. 1 and 2 there is illustrated therein a structure which includes a plastic sheet means 10. This plastic sheet material 10 may be Mylar for example. It is relatively thin and springy. Thus the plastic sheet means 10 in the illustrated example will preferably have a thickness which is on the order of 0.002 inch. In the illustrated example the sheet means 10 has a width which may be on the order of 1 inch and a length which may be on the order of 3 or 4 inches.

The sheet means 10 has opposed ends shown at the right and left in FIG. 1 and opposed faces which are directed upwardly and downwardly as viewed in FIG. 2, the upwardly directed face being covered with a nutrient layer 12 which is preliminarily sprayed onto the plastic 10 which forms a carrier for the nutrient layer 12. This nutrient layer 12 is extremely thin being hardly more than 0.001 inch in thickness and is sprayed or otherwise deposited on at least one surface of the sheet means 10. The composition of the nutrient layer forms no part of the present invention. This layer will preferably be a nutrient agar the composition of which is suitable for growth of a culture from a microorganism whose presence is suspected in a cavity of a body of a living being.

According to one of the features of the present invention the plastic sheet means 10 is formed with a number of small protuberances 14 respectively situated at the regions of the opposed edges of the sheet means 10 and respectively projecting from one of the opposed faces thereof. These protuberances are formed integrally with the sheet means 10 in any suitable manner. For example, small droplets of the plastic material while it is in a fluid, unsolidified condition, can be deposited on opposed faces of the sheet means 10 at the region of the ends thereof so that upon solidification the droplets form protuberances which adhere to and are in fact integral with the sheet means 10. However, these protuberances 14 can be formed in any suitable manner. They need not necessarily be regularly arranged as illustrated. If desired, for example, a suitably grooved cutting wheel such as a grinding wheel can be applied to the opposed edges of the flat sheet material 10 in order to form teeth at these opposed ends and the opposed edges can be angled in opposite directions to form rows of teeth projecting in opposite directions from the opposed faces of the sheet means 10. Any construction where protuberances are situated at the regions of the opposed edges of the sheet means 10 will suffice. It is only important that the height of the protuberances 14 be greater than the thickness of the nutrient layer 12 as will be apparent from the description which follows.

Although it is not absolutely essential in all cases in the illustrated example a wick layer 16 is shown engaging the nutrient layer 12 in the manner illustrated. This wick layer 16 may be a thin layer of cotton wadding or the like capable of absorbing a fluid by capillary action. The wick layer 16 engages part of the nutrient layer 12 and projects beyond one edge of the nutrient layer so that a fluid drawn into the body of the wick layer 16 will engage the nutrient layer 12. The plastic sheet means 10 is preferably provided with the integral protuberances 14 prior to spraying of the nutrient layer 12 thereon.

Figure 4:
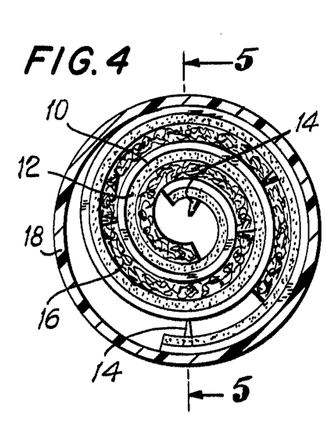
FIG. 4 is an end view of the structure of FIGS. 1 and 2 assembled with the structure shown in FIG. 3.

The above-described structure of FIGS. 1 and 2 is wound so as to have a spiral configuration, and the direction of winding is preferably such that the nutrient layer 12 becomes situated along the concave surface of the wound sheet material while the opposed convex surface thereof is directed away from the nutrient. The wound sheet means 10 with the nutrient layer thereon is illustrated in FIG. 4. It will be apparent from FIG. 4 that the protuberances 14 form a spacer means which prevents the turns from engaging each other. Thus, the protuberances 14 at one edge of the spiral strip will engage an adjoining turn in such a way as to maintain the turns spaced from each other in the manner illustrated in FIG. 4.

The structure which is thus wound into the spiral configuration is maintained in its spirally wound condition in any suitable way as by being situated in a suitable hollow cylindrical tube 18 made of any suitable plastic, for example, and having one open end and an opposite hemispherical hollow closed end in which air is trapped. Due to the springy nature of the plastic sheet material it will remain frictionally assembled with the tube 18.

Figure 5:
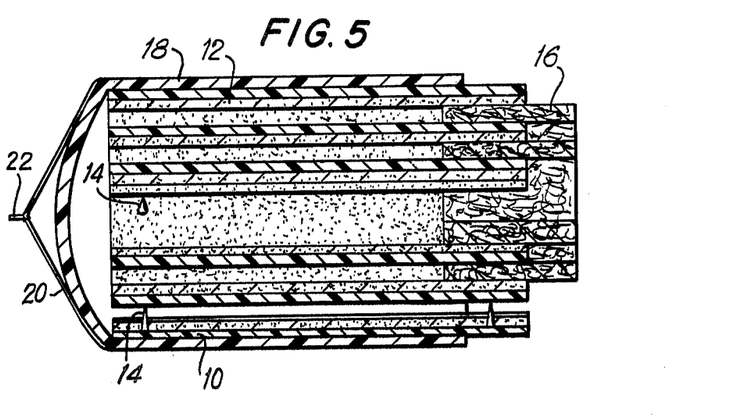
FIG. 5 is a longitudinal sectional elevation of the structure of FIG. 4 taken along line 5—5 of FIG. 4 in the direction of the arrows.

As is apparent from FIGS. 3 and 5 any suitable elongated flexible filamentary structure 20 such as a suitable string or the like is fixed in any suitable way to one end of the tube 18, as by being bonded thereto, and this string has a free end region 22 accessible to be grasped for withdrawing the assembly shown in FIGS. 4 and 5 out of a body cavity after it has remained therein for a length of time sufficient for a culture growth to develop to an extent adequate for rendering microorganisms visible if indeed they are present. As may be seen from FIG. 5 the wick 16 also becomes wound and projects freely beyond the nutrient layer so as to engage a fluid which by capillary action travels into engagement with the nutrient layer to spread therealong and to enable the microorganisms to travel into and become distributed over the nutrient layer enabling colonies of the microorganisms to grow if the suspected microorganisms are present.

The above-described structure of FIGS. 1-5 may be situated in any body cavity where the presence of microorganisms of a given disease is suspected. The particular example set forth above is suitable for insertion into the vagina, and upon being inserted in this way with the wick 16 being inserted first as the leading end of the assembly, the wick 16 may engage, for example, the cervix so that fluid at the cervix will be drawn by capillary action into the body of the wick 16 to engage the nutrient. However, any fluid present in the vagina will be contacted by the nutrient so that microorganisms of gonorrhea, vaginitis or other diseases which occur in the vagina can be detected from this construction.

As was indicated above, the wick 16 is not absolutely essential. For example the spaces between adjoining turns can be small enough to cause certain fluids to travel by capillary action into the spaces between the turns without the use of a wick.

In any event, with the above-described structure of the invention the nutrient layer 12 is maintained exposed to the oxygen-containing air, particularly as a result of the means 14, so that in this way where microorganisms will grow in oxygen, which is true, for example, of gonorrhea organisms, such microorganisms will readily grow in the nutrient layer.

After the article shown in FIGS. 4 and 5 has remained in a body cavity for a length of time sufficient for the microorganism to grow in the nutrient to an extent adequate to render the microorganism visible under a microscope, for example, the device is removed, and the string 20, 22 facilitates such removal. Then the carrier 10 together with the nutrient layer 12 carried thereby are removed from the tubular holder 18 so that the layer 12 becomes readily visible. At this time suitable staining with suitable dyes may be carried out so as to render the microorganisms clearly visible if indeed they are present.

In the case of gonorrhea, a suitable dye takes the form of a solution of P-aminodimethylaniline.

After such staining the nutrient on the plastic sheet material 10 is placed under a microscope, and it will be noted that in fact the configuration of the sheet 10 and the nutrient 12 thereon shown in FIGS. 1 and 2 does not differ greatly from the configuration of a conventional slide on which a specimen is placed to be examined under a microscope.

Thus, with the article described above it becomes easily possible to check for the presence of certain microorganisms, which require oxygen for optimum growth, directly in a body cavity where the microorganisms are grown under conditions precisely the same as those which obtain in the body cavity. The time required for microorganisms if they are present to grow sufficiently to become readily visible with the naked eye or under the microscope is well known in advance, so that the article is permitted to remain in the body cavity for a predetermined length of time required for such growth to occur. Because the device is not permitted to remain in the body for a longer period of time, there is no danger of encouraging the growth of disease microorganisms in the body to cause undesirable infection.

The nutrient layer 12 may have any desired composition which will show the presence of suspected microorganisms. When it is desired to check for the presence of different microorganisms, it is possible to make such a check for different microorganisms simultaneously by utilizing an arrangement as shown, for example in FIG. 6. Thus, referring to FIG. 6 there is illustrated therein a tampon 24 which can have the same general shape and size as a tampon conventionally used by women during menstruation. However, the tampon may be in the form of any soft covering enabling the structure to be situated anywhere in the body. In accordance with a further feature of the invention a number of the devices described above, without the wick 16 and the string 20, 22 are incorporated into the body of the tampon 24. Thus, FIG. 6 shows three such devices 26 embedded in the body of the tampon, which, as is conventional, includes a string 28 enabling the tampon to be conventionally withdrawn from the vagina. Thus, the several articles 26 will have a construction identical with that described above except that the wicks 16 are not used and the string 20, 22 are not used. The wadding which forms the tampon 24 has a density which enables air to flow freely throughout the interstices between the fibers which form the wadding, and thus fluids encountered in the vagina, for example, will impregnate the wadding and contact the nutrient layers 12 of the several articles 26. By providing different compositions for these nutrient layers it is possible to check simultaneously for the presence of different microorganisms, so that after the tampon 24 is withdrawn the coiled sheet material components can be removed from the tubes 18 to uncover the nutrient layers which then can be stained and inspected under the microscope as described above. In this way it becomes possible to check simultaneously for a number of different microorganisms.

Figures 7, 22:
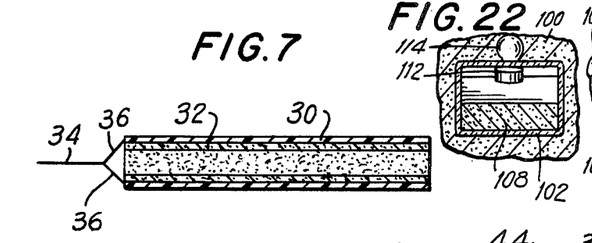
FIG. 7 is a schematic longitudinal sectional elevation of a further embodiment of a device according to the invention.
FIG. 22 is a transverse section of the structure of FIG. 21 taken along the line 22—22 of FIG. 21 in the direction of the arrows.
Figures 8, 9, 10, 11, 12, 23, 24, 25:
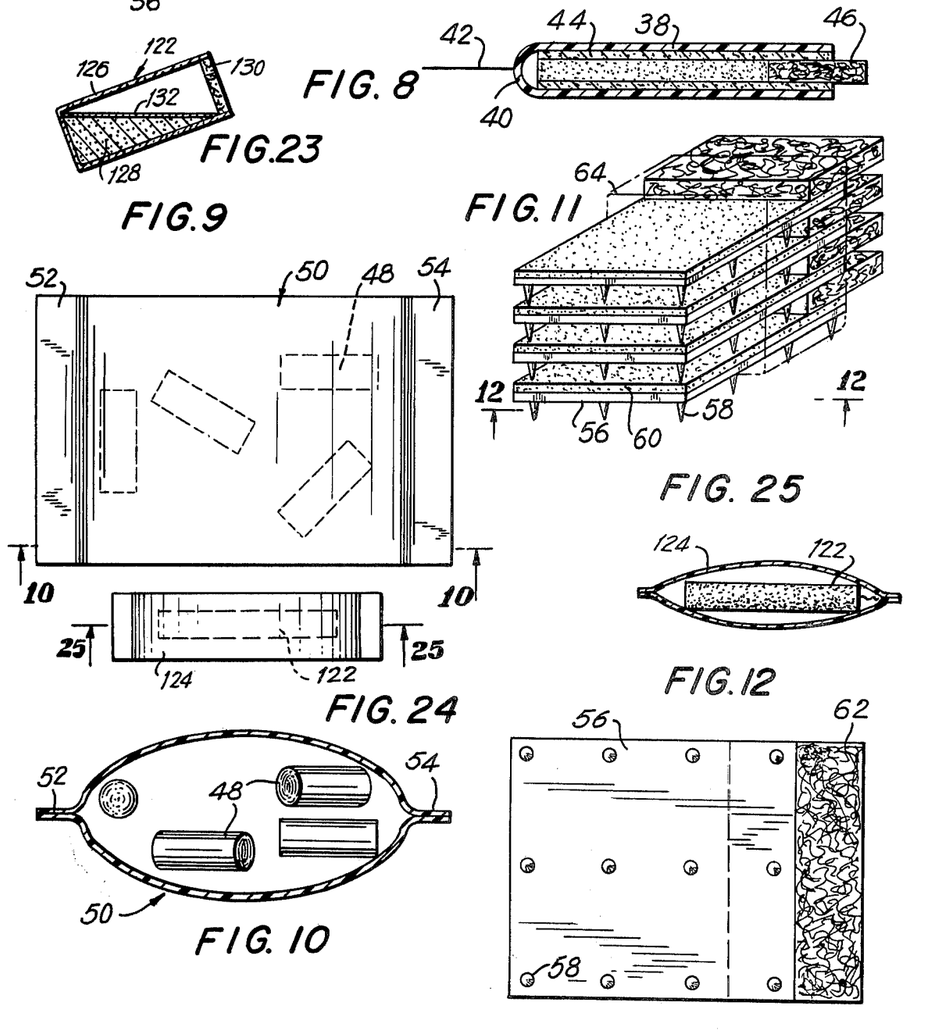
FIG. 8 is a longitudinal sectional elevation of a variation of the device in FIG. 7.
FIG. 9 is a plan view of a package of the invention containing articles of the invention.
FIG. 10 is a longitudinal sectional elevation of the structure shown in FIG. 9, taken along line 10—10 of FIG. 9 in the direction of the arrows.
FIG. 11 is a schematic perspective illustration of a further possible embodiment of a device according to the invention.
FIG. 12 is a schematic upwardly directed plan view of part of the structure of FIG. 11 taken along line 12—12 of FIG. 11 in the direction of the arrows.
FIG. 23 is a fragmentary longitudinal sectional elevation of a still further embodiment of a structure of the invention for growing microorganisms in a predetermined atmosphere.
FIG. 24 is a longitudinal elevation of a further embodiment of the invention for enabling microorganisms to be grown in the body in a predetermined atmosphere.
FIG. 25 is a longitudinal section of the structure of FIG. 24 taken along line 25—25 of FIG. 24 in the direction of the arrows.

Although the vagina has been referred to above as one example of a body cavity which may receive the article of the invention for carrying out the method of the invention, it is to be understood that the article and method of the invention may be utilized in any suitable body cavities. Some body cavities have an extremely restricted interior space, and for this purpose an article and method as illustrated in FIGS. 7 and 8 may be used in accordance with the invention. The article and method of the invention which is illustrated in FIGS. 7 and 8 is particularly adapted for use in the male urethra. For example, in the case of gonorrhea, it has recently been discovered that males as well as females can be carriers of gonorrhea without knowing this fact. Thus, it is highly desirable when a male is suspected of being a carrier of gonorrhea to check for the presence of gonorrhea microorganisms in the interior of the male urethra. For this purpose the structure as shown in FIG. 7 may be used. This structure includes an outer tube 30 made of any suitable transparent plastic material. This tube 30 will have an outer diameter on the order of 1/32 inch, and it may have a length on the order of 1 or 2 inches. The tube 30 is preferably flexible although for the relatively short length thereof it may also be substantially rigid, and the plastic material which forms the transparent tube 30 may be any readily available plastic which is neutral with respect to the interior of the body cavity such as the interior of the male urethra. For example, the tube 30 may be made of polyethylene or polypropylene, and similar materials may be used for the tube 18 shown in FIG. 3.

The tube 30 carries at its inner surface a layer or nutrient agar 32, and the thickness of this layer is extremely small, as was the case with the nutrient layer 12. Any small plug of cotton wadding or the like may be impregnated with the nutrient material which is still in a liquid condition and pushed through and beyond the tube 30 so as to deposit at the inner surface thereof a nutrient layer 32. In the example of FIG. 7 the opposed ends of the tube 30 are open, and a string 34 may have a pair of end portions 36 bonded to the tube 30 to facilitate withdrawal thereof.

This construction which is shown in FIG. 7 is introduced in a known way into the male urethra. The diameter of the passage defined by the inner surface of the nutrient layer 32 is sufficiently small to assure contacting of the nutrient layer 32 with fluids encountered in the interior of the urethra as a result of capillary action.

After the structure of FIG. 7 has remained in the male urethra for a length of time sufficient for microorganisms of suspected diseases, if they are present, to grow to an extent adequate to render such microorganisms readily visible in the nutrient, the structure of FIG. 7 is withdrawn from the body cavity. Because the tube 30 is transparent and because the nutrient layer 32 is extremely thin, it is possible to inspect for the presence of microorganisms directly through the wall of the tube 30 which is placed under a suitable microscope for this purpose. Of course any dyes required for staining purposes to render the microorganisms more readily visible can be applied to the nutrient layer 32 before it is inspected by eye. For this purpose a spray of a suitable staining liquid can be permitted to enter through the passage defined by the nutrient layer 32, this stain spreading itself over the nutrient layer to render microorganisms more readily visible if indeed they are present.

According to the variation which is shown in FIG. 8, the plastic tube 38 is identical with the tube 30 except that it has a closed end 40 to which a string 42 is connected for convenience of withdrawal. The nutrient layer 44 in this embodiment may be identical with the nutrient layer 32. At the open end of the assembly a small wick 46 is provided in the manner shown in FIG. 8 to assure that a fluid which carries a suspected microorganism will be drawn by capillary action into engagement with the nutrient layer 44.

As was pointed out above, the article of the invention may be utilized in any body cavities where it is desired to check for the presence of suspected microorganisms. Although the vagina and male urethra have been referred to above, it is apparent that the method and article of the invention may be used in other body cavities. For example the size and configuration provided for the article of the invention can readily be adapted for use in the interior of the ear, in the mouth, implanted between the gums and the teeth for example, in a nasal passage, or in any wound in the body which has been created accidentally or intentionally. The tampon type of device which is shown in FIG. 6 is particularly suitable for use in the rectum where a number of different microorganisms are highly likely to be present, so that this particular arrangement enables simultaneous checking for a number of different microorganisms to be readily carried out in a body cavity such as the rectum.

In order to assure the best possible conditions for growing cultures, it is important for the nutrient layer to be in a moist condition. If the nutrient layer becomes too dry, it is not possible to grow a culture under optimum conditions. One of the problems encountered with nutrient layer is that they tend to dry out excessively prior to use thereof. In order to avoid this latter undesirable condition, in accordance with the invention the articles which may be any of the articles described above and which are generally indicated at 48 in FIGS. 9 and 10, are situated in a package 50 constructed also in accordance with a further feature of the invention. Thus, the package 50 is made of a plastic or foil sheet material which is impervious to moisture. For example, the package 50 may be made of polyethylene sheet material. A tube of this sheet material having a length, for example, as illustrated in FIG. 9 is heat sealed or otherwise fluid-tightly closed at one end such as the end 52 shown at the left in FIGS. 9 and 10. While the opposed end 54 is still open the articles 48 of the invention are introduced. One or more of these articles having any of the above-described constructions, for example, may be situated in the interior of the enclosure which forms the package 50. In accordance with a particular feature of the present invention the end 54 of the package 50 is closed, as by heat sealing, in an atmosphere which contains a predetermined amount of moisture. For example before the container 50 is closed with one or more of the articles 48 therein, this container 50 is placed in an atmosphere which at room temperature has a 50% moisture content. Then the end 54 is closed as by heat sealing. In this way, the sealed enclosure formed by the package 50 can be maintained at ambient temperature with a sufficient amount of moisture sealed in the interior of the package to prevent the nutrient layers from drying out. Such packages can be stored at ambient temperatures in any suitable location for a considerable length of time prior to actual use of one or more of the articles 48, and in this way it is assured that the nutrient layer will be in the best possible condition for culture growth when the article is used. Of course, the above reference to a 50% moisture content of the atmosphere at room temperature is given only by way of example. Depending upon the nature of the nutrient it may be desirable to vary considerably from this particular value. For example, with some nutrients it may be desirable to have an atmosphere which is 75 or 80% moisture at room temperature prior to closing and sealing of the package.

It is to be noted, as was pointed out above, that the article of the invention may have widely different sizes and configurations depending upon the particular use which is intended for the article. For example different body cavities will require different sizes and configurations for the article. One possible variation in the structure is illustrated in FIGS. 11 and 12 according to which separate layers of sheet material 56 which can have the same thickness as the sheet material 10 and which can be made of the same material are situated parallel to each other and can have a rectangular configuration of any desired size. These small plastic sheets 56 are formed integrally with protuberances 58 situated, for example, according to an arrangement as shown most clearly in FIG. 12 or by way of suitable corrugations the same effect as that achieved from the protuberances 58 can be provided. One face of each plastic sheet material section 56 carries a nutrient layer 60 which conforms to the nutrient layers described above. Thus, a number of these assemblies can be placed one above the other as shown in FIG. 11 with the protuberances 58 forming a spacer means which assures that the nutrient layers are maintained exposed to the outer oxygen-containing atmosphere. If desired, layers of wick material 62 may be situated in engagement with the nutrient layers, between a nutrient layer and the next sheet material layer, as shown in FIG. 11. Any binding tape or other holding device 64, shown in phantom lines in FIG. 11, may surround the assembly of plastic and nutrient sections, held apart by the spacer means 58, to maintain them assembled together in the unit which is introduced into a body cavity. Of course, one of the great advantages resulting from an arrangement as shown in FIGS. 11 and 12 is that the separate plastic sheets 56 can carry nutrient layers 60 of different compositions, extremely convenient to check simultaneously for a number of different microorganisms. The different sections of sheet material 56 will carry suitable designations imprinted thereon for example, for identifying the compositions of the different nutrient layers and the microorganisms which are to be checked at the different nutrient layers.

After an article of the type shown in FIGS. 11 and 12 has been situated for a suitable length of time in a body cavity, it is removed, the different sections are separated from each other, and the different layers of nutrient can then be checked under a microscope, for example, for the presence of suspected microorganisms, with suitable dye staining also being utilized, if desirable.

It is to be noted in connection with all of the embodiments referred to above that the special nutrient in the agar is not necessarily uniformly distributed in the agar. Thus according to a further feature of the invention the special nutrient is added to the agar so as to be distributed therethrough according to a varying density of increasing concentration. Thus, in the case of FIGS. 5 and 8, for example, the density or concentration will increase toward the closed end of the tube 18 or the tube 38, thus insuring that the microorganism will grow toward the closed end of the tube rather than back toward the body. In this way encouraging of further infection of the body, in the event that the infection is present, may be reliably avoided. Of course, this feature can be used with any of the embodiments of the invention.

Figure 13:
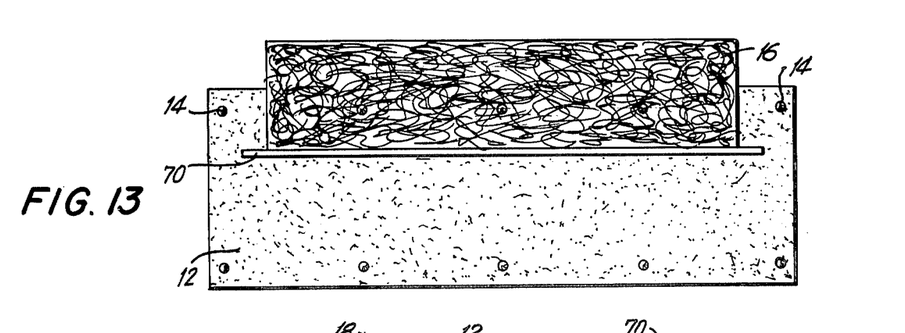
FIG. 13 shows a structure similar to FIG. 1 but provided with a wire for flattening the structure.
Figure 14:
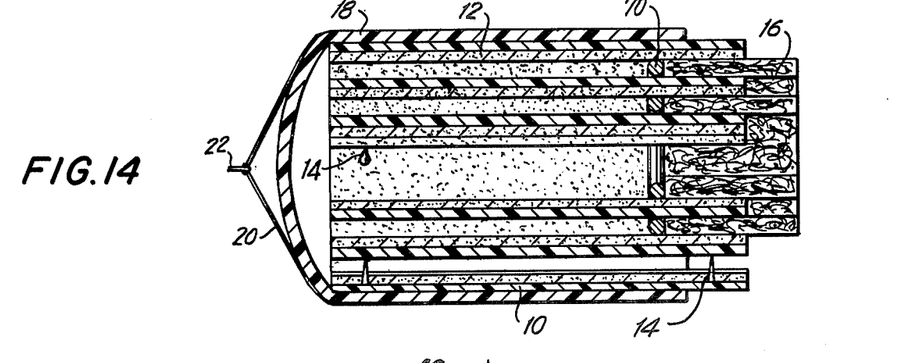
FIG. 14 is a schematic illustration of how the structure of FIG. 13 appears when it is wound into a spiral.

As has been indicated above, after a device such as that of FIG. 5 has been removed from the body, the coiled sheet material 10 is unwound so as to assume a flat condition for observation purposes. For the sake of convenience, this embodiment may be modified as shown in FIG. 13 according to which an elongated fine springy wire 70 is fixed with the plastic sheet material 10 for example along one edge of the wick 16. This very fine springy wire 70 may be made of any suitable metal and is adhered to the plastic of the sheet material 10 as by being fused thereto, although any suitable adhesive may also be used for this purpose. Thus, when the sheet material with the nutrient layer 12 thereon is coiled to assume the condition such as that illustrated in FIG. 14, this clearly takes place in opposition to the inherent springy force of the wire 70, so that when the wire 70 has the condition shown in FIG. 14 it is contributing to the maintenance of the convolutions in spaced relation with respect to each other and it is also constantly urging the coil back toward its flat condition. As a result when the sheet material 10 is removed from the tube 18 it will automatically assume its flat condition due to the springy characteristics of the wire 70, and thus a considerable convenience is achieved in this way with respect to absorbing the layer 12 in a flat condition.

Figure 15:
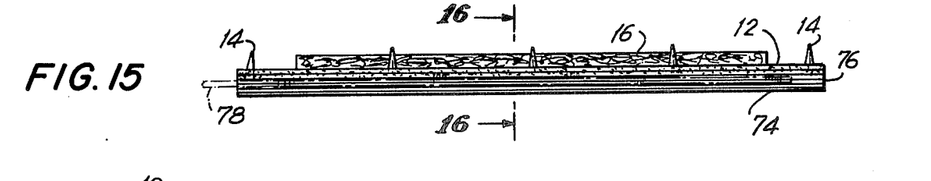
FIG. 15 is a schematic illustration of a further embodiment of the structure for rendering the latter flat for inspection purposes.
Figure 16:
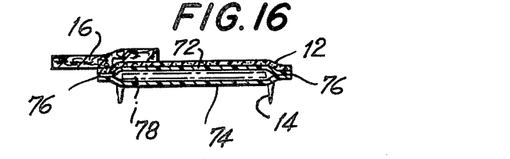
FIG. 16 is a transverse section of FIG. 15 taken along line 16—16 of FIG. 15 in the direction of the arrows, both FIG. 15 and FIG. 16 showing in phantom lines a blade which is to be used with the structure of FIGS. 15 and 16.

The same results may be achieved with an arrangement as shown in FIGS. 15 and 16. Thus, the structure shown in FIGS. 15 and 16 corresponds to the structure illustrated in FIGS. 1 and 2. The structure of FIGS. 15 and 16, however, differs from that of FIGS. 1 and 2 in that instead of a single sheet of plastic material 10, a pair of separate sheets 72 and 74 of the plastic material are used. The upper plastic sheet 72 shown in FIGS. 15 and 16 carries the nutrient layer 12 as well as the wick 16 and is provided at one end with the left protuberances 14, as viewed in FIG. 15. The lower sheet 74 carries at its right end, as viewed in FIG. 15, the downwardly directed protuberances 14. These sheets 72 and 74 are sealed to each other along their side edges 76, as illustrated in FIG. 16. Otherwise the sheets 72 and 74 are not connected to each other so that in effect they form an elongated flat sleeve which is open at its opposite ends. This structure with a single added sheet of plastic material need by only 0.001 inch thicker than a single sheet and thus it can readily be handled in the same way as the embodiment of FIGS. 1 and 2. However, with this construction in order to uncoil the plastic with the nutrient thereof when it is removed from an enclosure such as the tube 18, it is only necessary to introduce a metal blade 78, for example, as shown in phantom lines in FIGS. 15 and 16 into the space between the sheets 72 and 74 through one of the open ends of the sleeve which is formed thereby. This thin metal blade 78 will thus maintain the uncoiled structure in its flat condition rendering the structure extremely convenient to observe.

Figure 17:
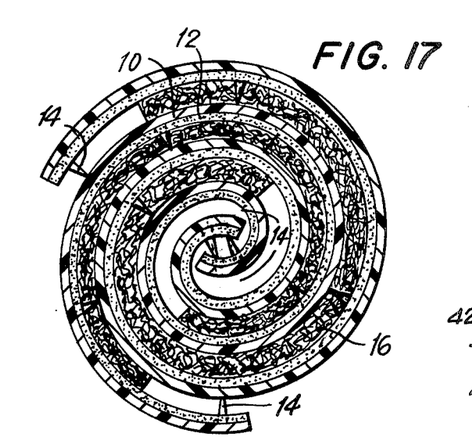
FIG. 17 is a schematic illustration of a variation according to which it is possible to provide a plurality of different components respectively carrying different mediums for detecting the presence of different microorganisms.

The arrangement as shown in FIG. 17 is similar to that of FIG. 4. The only difference is that a pair of structures as shown in FIG. 4 are interleaved with respect to each other. Thus, FIG. 17 illustrates a pair of plastic sheets 10 carrying the nutrient layers 12 and having the protuberances 14 precisely as described above in connection with FIGS. 1 and 2. However, in this case the pair of plastic sheets and the remaining structure are interleaved with each other as illustrated so as to form a pair of coils with the convolutions of one being situated between and spaced from the convolutions of the other. In this way it is possible to achieve with a construction of this type an arrangement where different nutrient layers of different positions are provided in the same unit in order to detect the presence of different microorganisms, achieving in this way a result similar to that achieved with the structure of FIGS. 11 and 12. Thus, it is possible to use a stack in the form of a sandwich type of construction, as shown in FIGS. 11 and 12 or interleaved coils, as shown in FIG. 17. Also it is to be noted that any of these structures such as that of FIGS. 5 and 11 may be situated in a cotton tampon-like holder when introduced into the body, providing a construction in the nature of that which is illustrated in FIG. 6.

Figure 18:
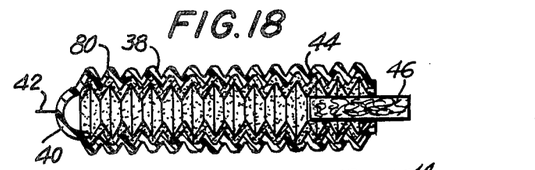
FIG. 18 is a variation of the structure of FIG. 8 according to which the outer casing is rendered more flexible.

Referring to FIG. 18, there is illustrated therein a construction similar to that of FIG. 8. However, in the case of FIG. 18 the outer tubular enclosure 80 which corresponds to the enclosure 38 is corrugated so as to have a high degree of flexibility. Otherwise the embodiment of FIG. 18 is the same as that of FIG. 8. As a result of the increased flexibility which is achieved in this way the device can be accepted by an individual without any particular discomfort. Thus a structure as shown in FIG. 18 can be received without any particular discomfort in the vagina and especially in the male urethra.

FIG. 19 illustrates a further embodiment of a structure to accomplish results similar to those accomplished by the structures of FIGS. 13, 15 and 16. Thus, according to FIG. 19 a member 90 which is flat, except at its ends 92, has between its ends a configuration conforming to an article such as that shown in FIG. 1. The ends 92 curved over the top surface of the member 90 as illustrated. When the coiled structure of FIG. 1 is removed from an enclosure 18 such as that of FIG. 5, the ends thereof can be slipped beneath the curved ends 92 of the plate 90, so that through this simple expedient the article can be maintained in its flat condition for convenience of inspection as described above.

Figure 20:
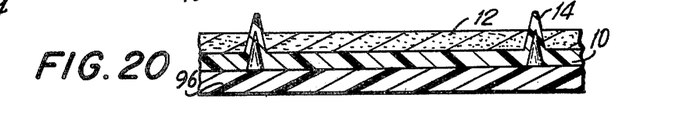
FIG. 20 is a fragmentary longitudinal sectional elevation of a further variation of the structure of FIGS. 1 and 2.

As is apparent particularly from FIG. 20, the protuberances 14 are tapered and hollow so that while they project from one face of the strip 10 they have open ends at the opposed face of the strip 10. As a result it is possible when the strip 10 is would that the protuberances of one coil might possibly be received in the hollow interior of the protuberances of the next coil. In order to avoid such entering of protuberances of one coil into the protuberances of the next coil, which would result in undesirably reducing the spacing between adjacent coils, the face or surfaces of the strip 10 where the open ends of the protuberances 14 are located has adhered thereto in any suitable way a strip or sheet of plastic material 96 which has the same size as the strip 10 and which effectively closes the open ends of the protuberances 14, as illustrated in FIG. 20. As a result, with this variation it will not be possible for any protuberances at one turn of the spiral to enter into protuberances of the next turn of the spiral and the maintenance of the desired spacing between the turns will be assured.

For the sake of simplicity all of the above discussion has been based on the assumption that the microorganisms will grow in an oxygen-containing atmosphere such as air. While it is true that many of the microorganisms to be detected will grow in air, there are also other microorganisms which will not grow in air or which will grow better in an atmosphere other than air. For example, it is known that *Neisseria gonorrhoeae*, which occurs at such inner body cavities as the vagina-cervix, anus-rectum, mouth-pharynx, or even in the eye, will grow very well in a carbon dioxide atmosphere which is preferable to air for this purpose. Thus, a microorganism of the latter type can be found in various different body areas as set forth above and it is to be understood that the structure of the invention can be situated in any body cavity, such as those referred to above, where the particular microorganism is suspected of being present.

Moreover, although it is possible to encounter the same microorganism in different body cavities, it is also possible to encounter a number of different microorganisms in the same body cavity with these different microorganisms having the same gaseous atmosphere requirements. Thus, *Neisseria gonorrhoeae, Neisseria meningitidis, Neisseria sicca* and *Neisseria catarrhalis* are facultated aerobes, in that they grow in an oxygen-containing atmosphere, but at the same time it is known that a $CO_2$ will greatly facilitate their growth, although such an atmosphere is not absolutely essential for their growth. The same type of $CO_2$ atmosphere will facilitate the growth of *Haemophilus ducreyi* and *Haemophilus vaginalis,* which are facultated anaerobes. Thus, microorganisms of this latter type prefer an atmosphere lacking oxygen for their growth, but nevertheless they will grow very well in a $CO_2$ atmosphere. *Streptococcus pyogenes* is another example of a facultated anaerobe. Micoplasma (PPLO) is a further example of a facultated aerobe. Of course, there are in addition microorganisms which are anaerobic so that they can only grow in atmospheres lacking in oxygen. Anaerobic Streptococci are such microorganisms. Furthermore, there are faculatated anaerobes which prefer to grow in atmospheres lacing in oxygen although they will grow in other atmospheres, Streptococcus pyogenes being an example of such microorganisms. Corynebacterium diphtheriae is an example of an aerobic microorganism which requires oxygen so that the above-described embodiments can be used in air to grow such microorganisms, *Mycobacterium tuberculosis* being a further example of an aerobic microorganism. An anaerobic microorganism example is Bacteroides which are found in the GI tract-colon, rectum, anus.

Thus, it is clear from the above that different types of predetermined atmospheres will provide essential or preferred growth conditions for different microorganisms, and in accordance with further features of the present invention the apparatus of the present invention will provide a predetermined atmosphere in the body cavity, this predetermined atmosphere being particularly suited for effective growth of a microorganism whose presence is suspected.

Figure 21:
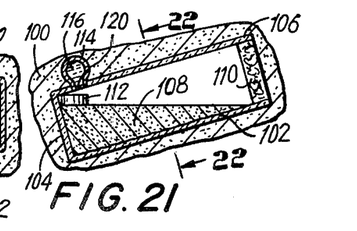
FIG. 21 is a fragmentary longitudinal sectional elevation of a further embodiment of the invention for enabling microorganisms to grow in a predetermined atmosphere, not necessarily air.

Referring to FIGS. 21 and 22, there is illustrated therein a further embodiment of the invention according to which a tampon 100 of cotton wadding or the like, of the type introduced into the vagina during menstruation, for example, has embedded in its interior a transparent tube 102 made of a clear plastic, for example. This tube 102 has a closed end 104 and an opposed open end 106. As is apparent from FIG. 22, the tube 102 is of a generally rectangular cross section and has flat walls, so that it is possible to look through a wall of the tube to observe the interior thereof without distortion which would be provided by a curved wall.

Within the tube 102 is situated a body 108 carrying a suitable nutrient. Thus this body 108 may be in the form of a well known agar provided with a suitable nutrient for the microorganisms. The open end 106 of the tube 102 is closed by a plug 110 which is actually a wick forming a means for placing the nutrient in the body 108 in contact with the body fluid. The wick 110 is itself made of a relatively dense cotton wadding or the like so that when the liquid such as blood, mucous or the like, is absorbed by the tampon 100, the liquid will engage the wick 110 and be drawn thereby through the wick 110 to contact the nutrient at the body 108.

Assuming, for example, that the microorganism is one which will grow very well in a carbon dioxide atmosphere, then it is desirable to situate in the interior of the tube 102 before it is closed by the plug 110 a pellet 112 which may be a simple bicarbonate pellet. The upper wall of the tube 102, as viewed in FIGS. 21 and 22 is formed with an opening which is closed by a flexible plastic container 114 having in its interior a liquid solution 116 such as a weak solution of acetic acid. The inner end 118 of the container 114, which closes an opening in the upper wall of the tube 102 as by being fused to the wall at its opening with a suitable solvent, or the like has an easily broken closure element 120 so that simply by squeezing the tampon 100 it is possible to break the closure 120 and permit the liquid 116 to engage the pellet 112. Thus, before the user of the device of FIGS. 21 and 22 inserts the tampon into the body cavity, the tampon will be squeezed so as to cause the liquid 116 to engage the pellet 112 with the result that carbon dioxide will be generated in the interior of the tube 102.

As a result it becomes possible to generate in the spaces over the body 108, which contains the nutrient, a $CO_2$ atmosphere in which certain microorganisms will grow very readily, as pointed out above.

Of course, there are other ways of providing in the interior of an enclosure such as the tube 102 a predetermined atmosphere. For example, as shown in FIGS. 24 and 25 it is possible to enclose an article 122 in a sealed enclosure 124 similar to that of the package 50 of FIG. 10. The article 122 can be identical with the structure shown in FIGS. 21 and 22 except that there is no pellet 112 and there is no flexible container 114 for a liquid 116. Instead the article 122 has a simple tube in which is located the body 108 with the nutrient carried thereby, the tube being closed at one end and having its open end closed by the plug 110 which forms a wick capable of placing the nutrient in contact with the body fluid which is suspected of having the particular microorganism therein. The article 122 is of course shown in FIG. 25 by itself, so that such an article can easily be placed at any desired body cavity, simply by inserting the plastic tube in such a way that the wick at the one end of the plastic tube will engage a body fluid.

When the article 122 is completed, and before the wick such as the wick 110 is used to close the open end of the tube, it is situated in an atmosphere which has the desired characteristics such as a carbon dioxide atmosphere or a nitrogen atmosphere. While thus situated in such an atmosphere the article is enclosed in a gas-tight manner in the enclosure 124. Such operations can be performed in the interior of an enlarged space which is closed off from the outer atmosphere and which contains the desired gas. In this way it is possible to seal in the enclosure 124 as well as in the tube of the article 122 a gas such as carbon dioxide or nitrogen. Carbon dioxide gas will be used instead of the embodiment shown in FIGS. 21 and 22, so that in this way it is not required to generate the gas. Nitrogen will be used for anaerobic or facultated anaerobic microorganisms, as referred to above. Since the atmosphere is filled with nitrogen, there will be no oxygen and such anaerobic or facultated anaerobic microorganisms will grow very well.

Thus, when using the device as shown in FIGS. 24 and 25, the closure 124 will be torn open and the article 122 will then be introduced into the body cavity. At this time the article 122 is of course filled with the gas such as carbon dioxide or nitrogen. Because the plug 110, which places the body fluid in contact with the nutrient, is relatively dense, it retards the flow of the gaseous atmosphere out of the interior of the tube, and since the article 122 will be maintained in the body cavity at the most for a period of a few hours, an assured growth of the microorganism in the required atmosphere is achieved.

A further embodiment of the invention is illustrated in FIG. 23. The article 122 shown therein may be identical with that shown in FIGS. 21 and 22. Thus, it has, as is the case with the article of FIGS. 21 and 22, a clear transparent tube 126 of plastic, for example, having in its interior the body 128 which corresponds in all respects to the body 108, one end of the tube 126 being closed and the other end being open, but plugged by the wick 130 which serves as the means to place the nutrient in the body 128 in contact with the body fluid.

It is to be noted that in all of the above embodiments it is possible to situate in the body 128 suitable fibers such as fibers of cotton or the like to engage the inner surface of the tube to increase the frictional contact therewith and thus retain the body 108 or 128 reliably in the interior of the tube. In addition it is possible to roughen the inner surface of the tube 102 or 126 so that further frictional holding of the body 128 against movement in the tube is achieved in this way, the surface at the interior of the tube being roughened at least at the area engaged by the body 128.

Furthermore, it is to be noted that in the embodiment of FIGS. 21 and 22 as well as in FIG. 23, and of course for the article shown in FIGS. 24 and 25, the body which carries the nutrient is inclined while being exposed to the inner space of the tube so that in this way a large area for growth is achieved.

With the particular embodiment which is shown in FIG. 23, a strip of filter paper 132 rests on the body 128 which contains the nutrient. The liquid which is drawn by the wick 130 into the interior of the tube 126 will have access through the filter 132 to the nutrient in the body 128, and the filter 132 will absorb the nutrient so that the microorganisms will grow directly on the filter 132.

The advantage which is achieved with the embodiment of FIG. 23 is that when the article is removed to check for the presence of the microorganisms, the plug 130 can be removed and the filter paper 132 can be removed so that it can be inspected apart from the tube 126. In this way if the surface of the tube 126 is rendered cloudy or otherwise affected so as to be obscure and render visibility in the interior of the tube difficult through a wall of the tube, the filter paper 132 nevertheless can be removed and directly seen either under the naked eye or under a microscope so as to check very effectively for the presence of the microorganisms.

It is thus apparent that with the above-described articles of the invention it becomes possible to check for the presence of one or more microorganisms in the case where these microorganisms are grown directly in the body cavity under the best possible conditions duplicating those which occur in the body cavity where the presence of the microorganisms is suspected, and at the same time the nutrient layers are maintained exposed to the required atmosphere in a highly reliable manner so that particularly for those microorganisms which grow best in an oxygen-containing atmosphere the method and article of the invention are highly suitable. The packaging feature shown in FIGS. 9 and 10 is of course applicable to any type of article which carries a material such as a culture medium which is to be prevented from drying excessively prior to use.

What is claimed is:

1. An article for growing a culture in a body cavity, comprising enclosure means, a nutrient for growing a microorganism in a given gaseous atmosphere in said enclosure means, support means for supporting said nutrient in said atmosphere and gaseous atmosphere generating means cooperating with the support means for providing a gaseous atmosphere to which the nutrient and microorganism will be exposed when the article is in said body cavity.

2. The article of claim 1 and wherein said support means includes a tube which carries said generating means, the latter being in the form of a means for generating carbon dioxide in the interior of said tube.

3. The article of claim 2 and wherein said means for generating carbon dioxide includes a bicarbonate pellet and a frangible container of acetic acid capable of being broken to release the acetic acid into contact with the tablet for generating carbon dioxide in the interior of said tube.

4. An article for growing a culture in a body cavity, comprising a nutrient for growing a microorganism in a given atmosphere, support means in the form of a sheet for supporting said nutrient in said atmosphere and means for cooperating with said support means for placing the nutrient in contact with a body fluid which may contain said microorganism, said support means and nutrient being wound to have a spiral configuration including a number of turns, and the nutrient being in the form of a layer and being carried by said support means and having a configuration corresponding to that of said support means, said support means for exposing the nutrient layer to said atmosphere further including spacer means carried by the support means for extending between a pair of turns to maintain them spaced from each other sufficient to expose the nutrient layer to a body fluid when said article is placed in a body cavity.

5. The combination of claim 4 and wherein said sheet is a plastic and said spacer means is in the form of relatively small protuberances integral with and projecting from a surface of the plastic sheet.

6. The combination of claim 5 and wherein said sheet is in the form of an elongated strip having a pair of opposed edges and a pair of opposed faces, and said protuberances including two groups of protuberances respectively situated at the regions of said edges and respectively projecting from one of the opposed faces of said sheet.

7. The article of claim 6 and wherein the nutrient layer and said protuberances are situated at one surface of said strip, said protuberances being tapered and hollow and having open ends at an opposed surface of said strip, and a sheet connected to and covering said opposed surface of said strip at least at said open ends of said protuberances so that if the protuberances of one turn are aligned with the open ends of the protuberances of another turn, said protuberances of said one turn will be prevented from entering into the protuberances of said other turn.

8. The combination of claim 6, and a holding means surrounding the support means for maintaining the latter wound in a spiral.

9. The article of claim 8 and wherein said holding means is in the form of an elongated tube which is closed at one end.

10. The article of claim 9 and wherein said tube is flexible and corrugated.

11. The combination of claim 4 and wherein a tampon carries in its interior the support means with the nutrient thereon.

12. The combination of claim 11 and wherein the tampon carries a plurality of said support means respectively carrying different nutrients for different microorganisms.

13. The combination of claim 4 and wherein said support means includes a plurality of layers of sheet material respectively carrying nutrient layers thereon, and said spacer means being situated between the layers of sheet material for spacing them apart from each other by a distance greater than the thickness of the nutrient layer.

14. The article of claim 13 and wherein said layers of sheet material are coiled and interleaved, with the nutrient layers respectively having different compositions for detecting the presence of different microorganisms.

15. The combination of claim 4 and wherein an enclosure means forms a package enclosing the support means with the nutrient thereon and with the means for placing the nutrient in contact with a body fluid, said enclosure means having an interior sealed off from the outer atmosphere and containing sufficient moisture to prevent drying of the nutrient.

16. The article of claim 4 and wherein an elongated springy wire is fixed to and extends along said sheet for returning the latter to a flat condition when it is not wound in a spiral configuration.

17. The article of claim 4 and wherein said sheet includes a pair of separate elongated layers of plastic sheet material having elongated side edges sealed to each other and defining between themselves an elongated sleeve which has opposed open ends so that a blade may be inserted through one of the open ends between the sheets to place them in a flat condition.

18. The article of claim 4 and wherein a flat plate with opposed curved end regions which define grooves at the ends of the flat plate is provided for receiving in said grooves ends of said sheet to maintain the latter flat for inspection of the nutrient layer.

19. A package comprising gas-tight enclosure means, at least one article for growing a culture in a body cavity, said article being situated in said enclosure means, and said article comprising a nutrient for growing a microorganism in a given gaseous atmosphere, and support means for supporting said nutrient in said gaseous atmosphere, and said gas-tight enclosure means having a given gaseous atmosphere in its interior closed off from the outer atmosphere, said gas-tight enclosure means providing in the article the given gaseous atmosphere to which the nutrient means and microorganism will be exposed when the article is removed from said enclosure means and placed in a body cavity.

20. The package of claim 19 and wherein for use in a male urethra, the article includes, as said support means, an elongated transparent plastic tube of a diameter sufficiently small to be introduced into the male urethra, and said nutrient being in the form of a nutrient layer carried by said plastic tube at an inner surface thereof and defining an interior hollow space into which a fluid in the urethra can enter so that if the fluid contains microorganisms which will grow in the nutrient, after a sufficient time the microorganisms will become evident in the nutrient, so that after the plastic tube is removed the presence of the microorganisms can be detected.

21. The package of claim 20 and wherein said tube is closed at one end and has fixed to said one end a string for removing the plastic tube after it has been introduced into the male urethra.

22. The package of claim 20 and wherein a wick engages the nutrient in the plastic tube at the region of at least one of the latter, said wick extending beyond the plastic tube to draw a fluid in a male urethra by capillary action into the interior of the plastic tube into engagement with the nutrient therein.

23. The package of claim 20 and wherein said plastic tube is flexible and corrugated.

24. The package of claim 19 and wherein said support means includes layers of sheet material which are flat and spacer means forming part of said support means and extending between the layers of sheet material thereof to form a sandwich-type of construction and said nutrient including layers carried by said layers of sheet material.

25. The package of claim 19 and wherein said given atmosphere has an amount of moisture sufficient to prevent drying of the nutrient prior to placing of the article in the interior of a body cavity where the body fluid is situated.

26. The package of claim 19 and wherein the microorganism is aerobic and the gas-tight enclosure means contains air.

27. The package of claim 19 and wherein the microorganism is anaerobic and the gas-tight enclosure means contains a gas which excludes oxygen.

28. The package of claim 27 and wherein the gas in said gas-tight enclosure means is nitrogen.

29. The package of claim 19 and wherein the microorganism grows best in a carbon dioxide atmosphere and said gas-tight enclosure means containing an atmosphere of carbon dioxide.

30. The package of claim 19 and wherein said support means includes a transparent tube having one closed end and opposed open end, said tube carrying in its interior a body containing said nutrient, and said body only partly filling the interior of said tube and having an exposed surface therein visible through a wall of said tube, and a plug closing said open end of said tube and having the construction of a wick engaging a part of said body, said tube enclosing said given atmosphere in the interior of said tube in contact with said nutrient-containing body, and said wick having a relatively great resistance to flow of gas therethrough for retarding the flow of said given atmosphere out of the interior of said tube.

31. The package of claim 30 and wherein said tube is of a generally rectangular cross section and has relatively flat walls through one of which an exposed surface of said body is visible.

32. The package of claim 31 and wherein said body has a minimum thickness at the region of said open end of said tube and is of a gradually increasing thickness toward the closed end of said tube where said body substantially extends across the entire interior of said tube, so that said body has an inclined surface extending from said closed end of said tube toward said open end thereof, and said surface being visible through a wall of said tube.

33. The package of claim 32 and wherein the microorganism grows best in carbon dioxide and said given atmosphere is composed at least partly of carbon dioxide.

34. The package of claim 32 and wherein the atmosphere contained in said tube is one which excludes oxygen while said microorganism is anaerobic.

35. The package of claim 34 and wherein said atmosphere is nitrogen.

36. The package of claim 30 and wherein the tube has an inner roughened surface engaging said body to prevent movement of the latter with respect to said tube.

37. The package of claim 36 and wherein said body contains fibers for coacting with the roughened inner surface of said tube for increasing the friction between said body and the inner surface of said tube.

38. The package of claim 19 and wherein said support means includes a tube having a closed end and an opposed open end, a body which contains said nutrient, being situated in the interior of said tube and only partly filling the latter with said body having out of engagement with the inner surface of said tube a surface which extends longitudinally along the interior of said tube, and a layer of filter paper carried by said surface of said body so that microorganisms will grow in the filter paper, and a plug closing said open end of said tube and engaging said body, said plug being in the form of a wick for forming said means for placing the nutrient in contact with the body fluid, so that when the article is removed from a body cavity after remaining therein for a time sufficient to grow said microorganism if it is present in the body fluid, the wick can be removed from the open end of the tube and the filter paper can then be removed for inspection to determine whether or not the microorganism is present in the body fluid.

* * * * *